(12) United States Patent
Cramp et al.

(10) Patent No.: US 6,642,418 B1
(45) Date of Patent: Nov. 4, 2003

(54) PROCESSES FOR PREPARING INTERMEDIATES

(75) Inventors: Susan Mary Cramp, Ongas Essex (GB); Neil Jonathan Geach, Ongas Essex (GB)

(73) Assignee: Aventis Cropscience SA (FR)

( * ) Notice: Subject to any disclaimer, the term of this patent is extended or adjusted under 35 U.S.C. 154(b) by 0 days.

(21) Appl. No.: 09/646,753

(22) PCT Filed: Mar. 22, 1999

(86) PCT No.: PCT/EP99/02335

§ 371 (c)(1),
(2), (4) Date: Dec. 4, 2000

(87) PCT Pub. No.: WO99/48851

PCT Pub. Date: Sep. 30, 1999

(30) Foreign Application Priority Data

Mar. 25, 1998 (GB) ............................................. 9806409

(51) Int. Cl.⁷ .................. C07C 45/00; C07C 49/23; C07C 69/76; C07C 69/74

(52) U.S. Cl. ................. 568/314; 568/319; 568/329; 568/338; 568/343; 568/346; 560/55; 560/118; 560/124

(58) Field of Search ................. 568/314, 319, 568/329, 338, 343, 346; 560/55, 118, 124

(56) References Cited

U.S. PATENT DOCUMENTS

| | | |
|---|---|---|
| 2,395,012 A | 2/1946 | Reeder et al. |
| 4,870,109 A | 9/1989 | Boisvenue et al. |
| 5,532,416 A | 7/1996 | Hamper et al. |
| 5,618,547 A | 4/1997 | Boisvenue et al. |
| 5,654,490 A | 8/1997 | Hamper et al. |
| 5,656,573 A * | 8/1997 | Roberts et al. |
| 5,707,930 A | 1/1998 | Felix et al. |
| 5,866,723 A | 2/1999 | Hamper et al. |
| 5,925,795 A * | 7/1999 | Felix et al. |

FOREIGN PATENT DOCUMENTS

| | | |
|---|---|---|
| EP | 0 418 175 A | 3/1991 |
| HU | 202 469 B | 9/1988 |
| HU | 217 299 B | 9/1997 |
| WO | WO 98 11046 A | 1/1998 |

OTHER PUBLICATIONS

Manfred Regitz, "Synthese von Diacyl–diazomethanen durch Diazogruppenubertragung", Chemische Berichte, vol. 99, pp. 3128–3147, 1966.

Suminori Umio et al., "Total Synthesis of Pyrrolnitrin VI Synthesis of Nitro–chloro–2–aminoacetophenones and 1–Aryl–1,3–butanediones", Chem. Pharm. Bull., vol. 17, pp. 596–604, 1969.

Alfred H. Frye et al., "A Contribution to the Structure of Citrinin", J. Org. Chem. vol. 14, pp. 397–404, 1949.

* cited by examiner

*Primary Examiner*—Samuel Barts
*Assistant Examiner*—Sikarl A. Witherspoon
(74) *Attorney, Agent, or Firm*—Connolly Bove Lodge & Hutz LLP

(57) ABSTRACT

The invention relates to processes for the preparation of compounds of formula (I), wherein $R^1$ and $R^2$ are as defined in the description.

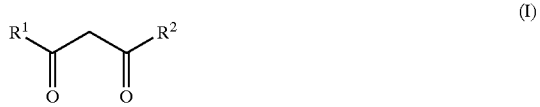

(I)

20 Claims, No Drawings

PROCESSES FOR PREPARING INTERMEDIATES

"This application is a 371 of PCT/EP99/02335, filed Mar. 22, 1999, and published as WO 99/48851 on Sep. 30, 1999".

This invention relates to novel processes for preparing intermediates (particularly beta keto ester and 1,3-dione compounds) useful in the manufacture of pesticides.

Pesticidal 4-benzoylisoxazoles, particularly 5-cyclopropylisoxazole herbicides and intermediate-compounds in their synthesis, are described in the literature, for example in European Patent Publication Nos. 0418175, 0487353, 0527036, 0560482, 0609798 and 0682659.

Various methods for preparing these compounds are known. The present invention seeks to provide improved or more economical methods for the preparation of pesticides and the intermediate compounds useful in preparing them. The present invention accordingly provides a process (A) for the preparation of a compound of formula (I):

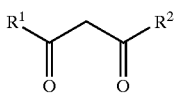
(I)

wherein:
one of the groups $R^1$ and $R^2$ is cyclopropyl and the other is phenyl substituted by two or three groups, which may be the same or different, selected from halogen, nitro, cyano, —$(CR^4R^5)S(O)_pR^6$, —$S(O)_pR^6$, $C_{1-6}$alkoxy, $C_{1-4}$haloalkoxy, $C_{1-4}$alkyl, $C_{1-4}$haloalkyl, 1,2,4-triazol-1-yl and —$SF_5$; wherein:
p is zero, one or two;
$R^4$ and $R^5$ are independently hydrogen or $C_{1-4}$alkyl; and
$R^6$ is $C_{1-4}$alkyl; which process comprises the hydrolysis and decarboxylation of a compound of formula (II):

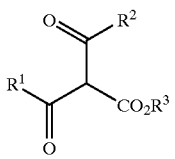
(II)

wherein $R^1$ and $R^2$ are as hereinbefore defined and $R^3$ is $C_{1-4}$alkyl.

Certain compounds of formula (I) are known and a number of processes for their preparation and conversion into herbicidal 4-benzoylisoxazole derivatives have been described in the European Patent Applications cited above.

In formulae (I) and (II) and in the formulae depicted hereinafter, preferred values of the symbols are as follows:

Preferably the group $R^1$ or $R^2$ which is substituted phenyl is substituted by two or three groups selected from halogen, trifluoromethyl, nitro, —$CH_2S(O)_pCH_3$, —$S(O)_pCH_3$, methoxy, methyl and 1,2,4-triazol-1-yl.

More preferably the group $R^1$ or $R^2$ which is substituted phenyl has as one of the substituents a 2-$S(O)_pCH_3$ group.

More preferably the group $R^1$ or $R^2$ which is substituted phenyl is selected from:
2-$S(O)_pCH_3$-4-$CF_3$; 2-$S(O)_pCH_3$-3-$OCH_3$-4-F; 2-$CH_2S(O)_pCH_3$-4-Br; 2-(1,2,4-triazol-1-yl)-4-$CF_3$; and 2-$NO_2$-4-$S(O)_pCH_3$ substituted phenyl.

Most preferably the group $R^1$ or $R^2$ which is substituted phenyl is selected from:
2-$S(O)_pCH_3$-4-$CF_3$; and 2-$S(O)_pCH_3$-3-$OCH_3$-4-F substituted phenyl.

Preferably $R^3$ is methyl or ethyl.

The preparation of compounds of formula (I) from compounds of formula (II) may be effected in a polar or a non-polar solvent (polar solvents are preferred). Preferably the solvent is water miscible. Examples of polar solvents include nitriles, particularly acetonitrile; dimethyl sulphoxide; dimethyl formamide; N,N-dimethylacetamide; N-methyl pyrrolidone; and ethers particularly dioxane and tetrahydrofuran. Acetonitrile is a preferred solvent for process (A). Examples of non-polar solvents include aromatic or aliphatic hydrocarbons, for example toluene and xylenes; or aromatic or aliphatic halogenated hydrocarbons, for example chlorobenzenes. The presence of water in the solvent medium is generally required. The amount of water may vary from catalytic to a large excess and it may be used as a co-solvent. The ratio of solvent/water is preferably from about 99.9:0.1 to about 9:1 (by volume).

Generally the reaction temperature used is from 0° C. to the boiling point of the solvent, preferably from 20° C. to 120° C., and more preferably from 60° C. to 100° C.

Generally the reaction takes place in the presence of a strong acid, usually a mineral acid, for example sulphuric acid or preferably hydrochloric acid, or an organic carboxylic acid such as trifluoroacetic acid. The amount of acid which is present can vary from a catalytic quantity to a large excess. Generally a catalytic amount gives good results.

By performing the reaction using acidic conditions and readily available reagents, the compounds of formula (I) may be obtained conveniently and in high yield with minimal formation of by products. The reaction is particularly useful for lower alkyl esters of formula (II), especially those where $R^3$ represents methyl or ethyl, because these compounds may be prepared from more readily available or less expensive starting materials.

According to a further feature of the present invention there is provided a process (B) for the preparation of a compound of formula (II) which comprises the acylation of a compound of formula (III):

(III)

wherein $R^1$ and $R^3$ are as hereinbefore defined, with a compound of formula (IV):

$R^2C(\!\!=\!\!O)X$ (IV)

wherein $R^2$ is as hereinbefore defined, and X is a leaving group, generally a halogen atom (preferably chlorine); or an imidazol-1-yl group.

In formulae (III) and (IV) the above preferred values for $R^1$ and $R^2$ are as hereinbefore defined for formulae (I) and (II).

In a particularly preferred aspect of the process (B), the group $R^1$ represents cyclopropyl; $R^2$ represents 2-$S(O)_p$$CH_3$-4-$CF_3$ or 2-$S(O)_p$$CH_3$-3-$OCH_3$-4-F substituted phenyl; and $R^3$ represents methyl, ethyl or tert butyl.

Compounds of formula $R^2C(\!\!=\!\!O)X$ and their carboxylic acid precursors are generally known in the literature when $R^2$ is cyclopropyl, and when $R^2$ is substituted phenyl their preparation is generally described in the European Patent Applications cited above and related publications.

The preparation of compounds of formula (II) from compounds of formula (III) and (IV) may be effected (a) by reacting a metal enolate of the compound of formula (III) with an acylating agent (IV). The metal enolate is preferably a magnesium enolate and is prepared, generally in situ, by reaction of (III) with a magnesium alkoxide base preferably magnesium methoxide or ethoxide. When a magnesium alkoxide is used it is generally employed in an equimolar amount.

The reaction of compounds of formula (III) and (IV) may also be effected (b) in the presence of a magnesium halide and a base. The magnesium halide is generally magnesium chloride, bromide or iodide, (magnesium iodide being conveniently prepared in situ using magnesium chloride and an alkali metal iodide, preferably sodium iodide or potassium iodide). The base used may be selected from trialkylamines, such as triethylamine, and pyridine. The amount of magnesium halide used is generally 1 equivalent, and the amount of base used is generally from 1 to 2 equivalents, preferably 2 equivalents. The reaction temperature is generally from 0° C. to 100° C., preferably from 0° C. to 30° C.

When the above reaction is performed using a magnesium enolate a side reaction may occur in which the compound (IV) reacts with alkoxide which is present as part of the magnesium enolate complex (even after removal of all of the alkanol that may have been present when used as solvent), resulting in the alkanoyl ester of (IV). Although this is not usually a problem, depending upon the particular compound (IV) used, the side reaction can become important and lead to a reduced yield of (II). This problem is substantially avoided when the magnesium halide/base procedure referred to above is adopted.

Solvents suitable for the above process for the preparation of compounds of formula (II) include nitriles, preferably acetonitrile; aromatic hydrocarbons preferably toluene; chlorinated hydrocarbons, such as dichloromethane; chlorinated aromatic solvents such as chlorobenzene; and ethers such as tetrahydrofuran and 1,4-dioxan.

Compounds of formula (II) wherein $R^3$ represents $C_{1-3}$ alkyl are novel and as such constitute a further feature of the present invention.

According to a further feature of the present invention there is provided a process (C) for the preparation of a compound of formula (III) by the reaction of a compound of formula (V):

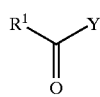 (V)

wherein $R^1$ is as hereinbefore defined, and Y represents a leaving group, for example cyano or preferably an optionally substituted imidazol-1-yl ring; with a compound of formula (VI):

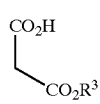 (VI)

wherein $R^3$ is as hereinbefore defined; to obtain, via the decarboxylation of an intermediate of formula (VII):

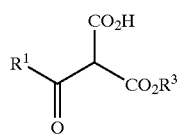 (VII)

wherein $R^1$ and $R^3$ are as hereinbefore defined, a compound of formula (III). The intermediate of formula (VII) is not generally isolated and is decarboxylated in situ in the presence of an acid.

In formulae (V), (VI) and (VII) the above preferred values for $R^1$ are as hereinbefore defined for formulae (I) and (II).

The imidazol-1-yl group Y is optionally substituted by from one to three (generally one or two) groups selected from $C_{1-4}$alkyl, $C_{1-4}$haloalkyl, and halogen. Preferably Y is imidazol-1-yl.

More preferably $R^1$ is cyclopropyl; or is selected from:
2-S(O)$_p$CH$_3$-4-CF$_3$-phenyl; and 2-S(O)$_p$CH$_3$-3-OCH$_3$-4-F-phenyl.

Most preferably $R^1$ is cyclopropyl.

Preferably $R^3$ is methyl, ethyl or tert butyl.

The preparation of compounds of formula (VII) from compounds of formula (V) or (VI) may be effected (a) by reacting a metal complex of the compound of formula (VI) with the compound of formula (V). The reaction is generally conducted under the conditions hereinbefore described for the reaction of compounds of formula (III) and (IV).

The reaction of compounds of formula (V) and (VI) may also be effected (b) in the presence of a magnesium halide and a base, generally under the conditions hereinbefore described for the reaction of compounds of formula (III) and (IV).

Solvents suitable for the above process for the preparation of compounds of formula (III) include those described above for the preparation of compounds of formula (II). Especially preferred solvents for process (C) are acetonitrile or tetrahydrofuran.

Optionally the compound of formula (V) may be generated in situ by reacting a compound of formula:

$$R^1C(=O)Cl \qquad (VIII)$$

with an 1H-imidazole optionally substituted by from one to three (generally one or two) groups selected from $C_{1-4}$alkyl, $C_{1-4}$haloalkyl, and halogen. Preferably the 1H-imidazole compound is unsubstituted. Generally 2 equivalents of the optionally substituted 1H-imidazole are used in the reaction which is conducted in an inert solvent, for example acetonitrile or tetrahydrofuran, at a temperature of from −20° C. to 60° C.

Alternatively the compound of formula (V) may be generated in situ by reacting a compound of formula:

$$R^1C(=O)OH \qquad (VIIIa)$$

with an optionally substituted 1,1'-carbonyldiimidazole derivative (preferably 1,1'-carbonyldiimidazole).

Equimolar amounts of (V):(VI) are generally employed.

The intermediates of formula (VII) which are beta ketoacids are decarboxylated, usually in situ in the presence of a strong acid, generally a mineral acid, preferably hydrochloric acid, and generally at a temperature of from 0° C. to 60° C. to provide the compounds of formula (III).

The process (C) to prepare compounds of formula (III) is particularly useful for preparing compounds wherein $R^1$ is cyclopropyl, and is more convenient than other known procedures, for example those involving acylation of the expensive Meldrum's acid (2,2-dimethyl-1,3-dioxan-4,6-dione) followed by alcoholysis and decarboxylation as described in European Patent Publication Number 0418175. An advantage of the process (C) for the preparation of compounds of formula (III) from imidazolides of formula (V) is that much higher yields of product are obtained as compared with the same reaction in which the imidazolide of formula (V) is replaced by acid chlorides of formula (VIII).

Compounds of formula (III) and (V) wherein the group $R^1$ is phenyl substituted by two or three groups one of which is 2-S(O)$_p$R$^6$ are novel and as such constitute a further feature of the present invention.

Compounds of formula (VI) are known.

According to a further feature of the invention processes (A) and (B) can be combined to prepare a compound of formula (I) from a compound of formula (III).

According to a further feature of the invention processes (A), (B) and (C) can be combined to prepare a compound of formula (I) from a compound of formula (V).

According to a further feature of the invention processes (B) and (C) can be combined to prepare a compound of formula (II) from a compound of formula (V).

The compounds of formula (I) obtained by the processes of the present invention may be used in the preparation of herbicidally active 4-benzoylisoxazole derivatives according to the following reaction schemes:

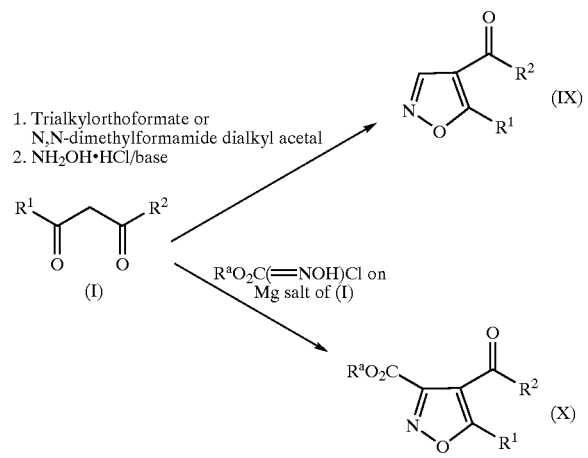

In the above schemes $R^1$ represents cyclopropyl, $R^2$ represents substituted phenyl and $R^a$ represents alkyl. The 4-benzoylisoxazoles of formula (IX) and (X) are described in for example European Patent Publication Nos. 0418175, 0487353, 0527036, 0560482, 0609798 and 0682659.

The following non-limiting examples illustrate the invention.

EXAMPLE 1

Preparation of 3-Cyclopropyl-1-(4-fluoro-3-methoxy-2-methylthiophenyl)propane-1,3-dione A solution of 3-cyclopropyl-1-(4-fluoro-3-methoxy-2-methylthiophenyl)-2-methoxycarbonyl-propane-1,3-dione (0.15 g) in a mixture of acetonitrile/water (95:5) containing 3 drops of hydrochloric acid (2M) was heated at reflux for 44 hours, cooled, dried (magnesium sulphate) and evaporated to give the title compound (0.08 g), NMR 0.9 (m, 2H), 1.1 (m, 2H), 1.65 (m, 1H), 2.37 (s, 3H), 3.96 (s, 3H), 4.15 (s, 1H), 5.9 (s, 1H), 6.95–7.15 (m, 2H).

The above compound was also prepared in a similar manner, but using acetonitrile without addition of water, from 3-cyclopropyl-2-ethoxycarbonyl-1-(4-fluoro-3-methoxy-2-methylthiophenyl)propane-1,3-dione. In this experiment the reaction mixture was heated for 20 hours at reflux, resulting in a clean conversion to the title compound (as shown by nmr), but after this time 60% of the starting ethyl ester still remained.

EXAMPLE 2

Preparation of 3-Cyclopropyl-1-(4-fluoro-3-methoxy-2-methylthiophenyl)-2-methoxycarbonylpropane-1,3-dione Carbon tetrachloride was added to a suspension of magnesium turnings (0.107 g, 1.1 equivalents) in methanol. A solution of methyl 3-cyclopropyl-3-oxopropanoate (0.395 g, 1.1 equivalents) in methanol was then added. The mixture was stirred at 60° C. for 0.5 hour, cooled, evaporated and re-evaporated after addition of dry toluene to give the corresponding magnesium enolate. To a toluene solution of half of this magnesium enolate was added a solution of 4-fluoro-3-methoxy-2-methylthiobenzoyl chloride (0.54 g) in toluene and the mixture stirred at 20° C. for 18 hours, washed (2M hydrochloric acid then with water), dried (magnesium sulphate) and evaporated to give the title compound (0.75 g), NMR 1.1 (m, 2H), 1.38 (m, 2H), 2.4 (s, 3H), 2.62 (m, 1H), 3.42 (s, 3H), 4.0 (s, 3H), 6.9 (m, 1H), 7.1 (m, 1H), 17.8 (s, 1H).

By proceeding in a similar manner starting from ethyl 3-cyclopropyl-3-oxopropanoate there was prepared:

3-cyclopropyl-2-ethoxycarbonyl-1-(4-fluoro-3-methoxy-2-methylthiophenyl)propane-1,3-dione, NMR 0.87 (t, 3H), 1.12 (m, 2H), 1.39 (m, 2H), 2.4 (s, 3H), 2.68 (m, 1H), 3.9 (q, 2H), 4.0 (s, 3H), 6.9 (m, 1H), 7.1 (m, 1H), 17.85 (s, 1H).

EXAMPLE 3

Preparation of 2-t-Butoxycarbonyl-3-cyclopropyl-1-(4-fluoro-3-methoxy-2-methylthiophenyl)propane-1,3-dione A solution of t-butyl 3-cyclopropyl-3-oxopropanoate (0.07 g, 1 equivalent) in acetonitrile was added to magnesium chloride (0.036 g, 1 equivalent) in acetonitrile with stirring under an inert gas. The mixture was cooled to 0° C. and pyridine (0.061 ml, 2 equivalents) added. After 4 hours at 0° C., a solution of 4-fluoro-3-methoxy-2-methylthiobenzoyl chloride (0.09 g) in acetonitrile was added. After 0.75 hour, water and hydrochloric acid (2M) were added, with extraction into ether. The extract was dried (magnesium sulphate) and evaporated to give the title compound (0.139 g), NMR 1.1 (m, 2H), 1.18 (s, 9H), 1.35 (m, 2H), 2.42 (s, 3H), 4.0 (s, 3H), 6.9 (m, 1H), 7.05–7.15 (m, 1H), 17.6 (bs,1H).

EXAMPLE 4

Preparation of t-Butyl 3-Cyclopropyl-3-oxopropanoate Using Magnesium Ethoxide as Base A solution of mono t-butyl malonate (0.525 g, 1 equivalent) in tetrahydrofuran was added to a mixture of magnesium ethoxide (0.357 g, 1 equivalent) in tetrahydrofuran and stirred at 20° C. for 4 hours. After cooling to 0° C. a solution of N-cyclopropanecarbonylimidazole (0.425 g, 1 equivalent) in tetrahydrofuran was added and the mixture stirred for 1 hour and then at 20° C. overnight. Hydrochloric acid (2M) was added and the mixture stirred for 0.5 hour, extracted (ether), dried (magnesium sulphate) and evaporated to give the title compound (0.519 g), NMR 0.95 (m, 2H), 1.1 (m, 2H), 1.3 (m, 1H), 1.5 (s, 9H), 3.5 (s, 2H).

EXAMPLE 5

Preparation of t-Butyl 3-Cyclopropyl-3-oxopropanoate Using Magnesium Chloride and Triethylamine as Base Mono t-butyl malonate (0.184 g, 1.2 equivalents) was added to a stirred mixture of dry magnesium chloride (0.084 g, 1.2 equivalents) in dry acetonitrile and cooled to 0° C. Triethylamine (0.204 ml, 2 equivalents) was added and stirred at 0° C. for 0.25 hour. N-Cyclopropanecarbonylimidazole (0.10 g, 1 equivalent) was added at 0° C. and stirring maintained for 1 hour at 0° C. then overnight at 20° C. Hydrochloric acid (2M) was added and the mixture extracted (ether), washed (2M sodium hydroxide solution then with water), dried (magnesium sulphate) and evaporated to give the title compound (0.05 g), NMR 0.95 (m, 2H), 1.1 (m, 2H), 1.3 (m, 1H), 1.5 (s, 9H), 3.5 (s, 2H).

COMPARATIVE EXAMPLE 5a

Preparation of t-Butyl 3-Cyclopropyl-3-oxopropanoate From Cyclopropanecarbonyl Chloride Using Magnesium Chloride and Triethylamine as Base By proceeding according to the above Example 5 but replacing N-cyclopropylcarbonylimidazole with cyclopropanecarbonyl chloride, analysis of the product obtained showed that none of the title compound had been formed.

The above experiment shows the clear advantage of using N-cyclopropylcarbonylimidazole as compared with cyclopropanecarbonyl chloride.

EXAMPLE 6

Preparation of t-Butyl 3-Cyclopropyl-3-oxopropanoate Using Magnesium Chloride and Triethylamine as Base Via In Situ Formation of N-Cyclopropanecarbonylimidazole Imidazole (0.143 g, 2.2 equivalents) and mono t-butyl malonate (0.141 g, 1.2 equivalents) were added to a stirred mixture of dry magnesium chloride (0.109 g, 1.2 equivalents) in dry acetonitrile and cooled to 0° C. Triethylamine (0.204 ml, 2 equivalents) was added and stirred for 0.25 hour, before addition of cyclopropanecarbonyl chloride (0.1 g, 1 equivalent) at 0° C. Stirring was continued for 1 hour at 0° C. and then overnight at 20° C. Hydrochloric acid (2M) was added and the mixture extracted (ether), washed (2M sodium hydroxide solution, then with water) and evaporated to give the title compound (0.111 g), NMR 0.95 (m, 2H), 1.1 (m, 2H), 1.3 (m, 1H), 1.5 (s, 9H), 3.5 (s, 2H).

REFERENCE EXAMPLE 1

Preparation of 4-Fluoro-3-methoxy-2-methylthiobenzoyl Chloride 2,4-Difluoro-3-methoxybenzoic acid (38.2 g) was added to a stirred solution of methyl mercaptan (9.7 g) in dry tetrahydroftran under an inert atmosphere. A solution of n-butyl lithium (162 ml of a 2.5M solution in hexane) was added dropwise at −78° C. After 1 hour the mixture was allowed to warm to 20° C. overnight and evaporated. Hydrochloric acid (2M) and ether were added and the organic phase washed (water), dried mil (magnesium sulphate) and evaporated. The residue was triturated with hexane to give 4-fluoro-3-methoxy-2-methylthiobenzoic acid (29.2 g), NMR 2.6 (s, 3H), 4.0 (s, 3H), 7.1 (m, 1H), 7.9 (m, 1H). oxalyl chloride (51.5 g) was added to a stirred solution of 4-fluoro-3-methoxy-2-methylthiobenzoic acid (29.2 g) in dichloromethane. After 3.5 hours the mixture was evaporated to give the title compound (33.0 g), used directly in the above reactions.

REFERENCE EXAMPLE 2

Preparation of N-Cyclopropanecarbonylimidazole

A solution of cyclopropanecarbonyl chloride (10.0 g) in dry tetrahydrofuran was added dropwise to a solution of imidazole (13.0 g, 2 equivalents) stirred at 0° C. After 1 hour the solid was filtered and the filtrate evaporated to give the title compound (13.3 g), NMR 1.2 (m, 2H), 1.38 (m, 2H), 2.21 (m, 1H), 7.12 (d, 1H), 7.55 (d, 1H), 8.34 (s, 1H).

COMPARATIVE EXAMPLE TO ILLUSTRATE THE UTILITY OF THE INVENTION

Preparation of 5-Cyclopropyl-4-(4-fluoro-3-methoxy-2-methylsulphonylbenzoyl)isoxazole A mixture of 3-cyclopropyl-1-(4-fluoro-3-methoxy-2-methylsulphonylphenyl)propane-1,3-dione (5.4 g) and triethylorthoformate (4.8 g) in acetic anhydride (4.5 g) was heated under reflux for 4 hours. The mixture was evaporated to give 3-cyclopropyl-2-ethoxymethylene-1-(4-fluoro-3-methoxy-2-methylsulphonylphenyl)propane-1,3-dione (6.1 g) as a red oil, which was used directly in the next stage.

By proceeding in a similar manner the following compound was also prepared:

3-cyclopropyl-2-ethoxymethylene-1-(4-fluoro-3-methoxy-2-methylthiophenyl)propane-1,3-dione.

Hydroxylamine hydrochloride (1.67 g) and sodium acetate (1.3 g) were added to a stirred solution of 3-cyclopropyl-2-ethoxymethylene-1-(4-fluoro-3-methoxy-2-methylsulphonylphenyl)propane-1,3-dione (6.1 g) in ethanol. After 1 hour the solvent was evaporated, and the residue in ethyl acetate was washed (water), dried (magnesium sulphate) and evaporated. Purification of the residue by column chromatography on silica gel eluting with ethyl acetate/hexane (1:1) and trituration with ethanol gave the title compound (1.4 g), m.p. 122–123° C.

By proceeding in a similar manner the following compound was also prepared:

5-cyclopropyl-4-(4-fluoro-3-methoxy-2-methylthiobenzoyl)isoxazole, m.p. 62.5–65° C.

What is claimed is:

1. A process for the preparation of a compound of formula (I):

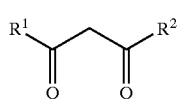

wherein:

one of the groups $R^1$ and $R^2$ is cyclopropyl and the other is phenyl substituted by two or three groups, which may be the same or different selected from halogen, nitro, cyano, —(CR⁴R⁵)S(O)$_p$R⁶, —S(O)$_p$R⁶, C$_{1-6}$alkoxy, C$_{1-4}$haloalkoxy, C$_{1-4}$alkyl, C$_{1-4}$haloalkyl, 1,2,4-triazol-1-yl and —SF$_5$; wherein:

p is zero, one or two;

R⁴ and R⁵ are independently hydrogen or C$_{1-4}$alkyl; and

R⁶ is C$_{1-4}$alkyl;

which process comprises the hydrolysis and decarboxylation of a compound of formula (II):

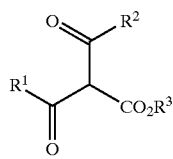
(II)

wherein R¹ and R² are as hereinbefore defined, and R³ is C$_{1-4}$alkyl, in the presence of water.

2. A process according to claim 1 which is performed in the presence of a strong acid.

3. A process according to claim 2 in which the acid is present in a catalytic amount.

4. A process according to claim 1 which is performed in a polar solvent.

5. A process according to claim 4 in which the polar solvent is acetonitrile.

6. A process according to claim 1 wherein the group R¹ or R² is substituted phenyl is selected from the group consisting of:

2-S(O)$_p$CH$_3$-4-CF$_3$; 2-S(O)$_p$CH$_3$-3-OCH$_3$-4-F; 2-CH$_2$S(O)$_p$CH$_3$-4-Br;

2-(1,2,4-triazol-1-yl)-4-CF$_3$; and 2-NO$_2$-4-S(O)$_p$CH$_3$ substituted phenyl.

7. A process according to claim 1 wherein the group R¹ or R² which is substituted phenyl is selected from the group consisting of:

2-S(O)$_p$CH$_3$-4-CF$_3$; and 2-S(O)$_p$CH$_3$-3-OCH$_3$-4-F substituted phenyl.

8. A process according to claim 1 wherein R³ is methyl or ethyl.

9. A process according to claim 1 in which the compound of formula (II) is prepared by acylating a compound of formula III:

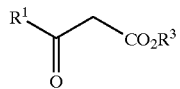
(III)

with a compound of formula (IV):

R²C(=O)X (IV)

wherein X is a leaving group.

10. A process for the preparation of a compound of formula (II):

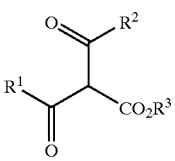
(II)

wherein one of the groups R¹ and R² is cyclopropyl and the other is phenyl substituted by two or three groups, which may be the same or different selected from the group consisting of halogen, nitro, cyano, —(CR⁴R⁵)S(O)$_p$R⁶, —S(O)$_p$R⁶, C$_{1-6}$alkoxy, C$_{1-4}$haloalkoxy, C$_{1-4}$alkyl, C$_{1-4}$haloalkyl, 1,2,4-triazol-1-yl and —SF$_5$; and R³ is C$_{1-4}$alkyl comprising acylating a compound of formula III:

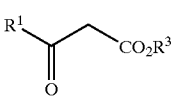
(III)

with a compound of formula (IV):

R²C(=O)X (IV)

wherein X is a leaving group, wherein said process is performed using a magnesium halide in the presence of a base.

11. A process for the preparation of a compound of formula (III):

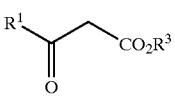
(III)

wherein R¹ is cyclopropyl or phenyl substituted by two or three groups, which may be the same or different selected from the group consisting of halogen, nitro, cyano, —(CR⁴R⁵)S(O)$_p$R⁶, —S(O)$_p$R⁶, C$_{1-6}$alkoxy, C$_{1-4}$haloalkoxy, C$_{1-4}$alkyl, C$_{1-4}$haloalkyl, 1,2,4-triazol-1-yl and SF$_5$; wherein:

p is zero, one, or two;

R⁴ and R⁵ are independently hydrogen or C$_{1-4}$alkyl; and

R⁶ is C$_{1-4}$alkyl; and

R³ is C$_{1-4}$alkyl, comprising reacting a compound of formula (V):

(V)

wherein Y is a leaving group, with a compound of formula (VI):

(VI)

via the decarboxylation of a compound of formula (VII):

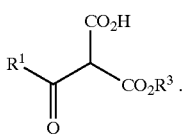
(VII)

12. A process according to claim 10, in which the compound of formula (III) is prepared by reacting a compound of formula (V):

(V)

wherein Y is a leaving group, with a compound of formula (VI):

(VI)

via the decarboxylation of a compound of formula (VII):

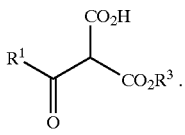
(VII)

13. A process according to claim 11 wherein $R^1$ represents cyclopropyl.

14. A process according to claim 11 wherein Y is imidazol-1-yl.

15. A process according to claim 11 wherein the compound of formula (VII) is decarboxylated in the presence of a strong acid.

16. The process of claim 11 wherein a metal complex of the compound of formula (VI) is reacted with a compound of formula (V).

17. The process of claim 16 in which the metal complex is a magnesium complex.

18. The process of claim 17 which is performed using a magnesium alkoxide base.

19. The process of claim 17 which is performed using a magnesium halide in the presence of a base.

20. A compound having the formula (II):

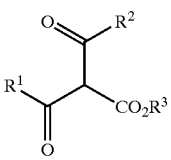
(II)

wherein one of the groups $R^1$ and $R^2$ is cyclopropyl and the other is phenyl substituted by two or three groups, which may be the same or different selected from the group consisting of halogen, nitro, cyano, —$(CR^4R^5)S(O)_pR^6$, —$S(O)_pR^6$, $C_{1-6}$alkoxy, $C_{1-4}$haloalkoxy, $C_{1-4}$alkyl, $C_{1-4}$haloalkyl, 1,2,4-triazol-1-yl and —$SF_5$; wherein:

p is zero, one, or two;

$R^4$ and $R^5$ are independently hydrogen or $C_{1-4}$alkyl; and $R^6$ is $C_{1-4}$alkyl;

and $R^3$ is $C_{1-3}$alkyl.

* * * * *